United States Patent [19]

Schoenwald

[11] Patent Number: 4,879,294

[45] Date of Patent: Nov. 7, 1989

[54] OPTHALMIC COMPOSITION

[75] Inventor: Ronald D. Schoenwald, Iowa City, Iowa

[73] Assignee: Angelini Pharmaceuticals Ltd., River Edge, N.J.

[21] Appl. No.: 149,249

[22] Filed: Jan. 28, 1988

[51] Int. Cl.⁴ .................... A61K 31/50; A61K 31/42; A61K 31/40
[52] U.S. Cl. .................................. 514/253; 514/374; 514/427; 514/912
[58] Field of Search ................ 514/374, 253, 912, 427

[56] References Cited

U.S. PATENT DOCUMENTS

| | | | |
|---|---|---|---|
| 2,727,846 | 12/1955 | Talbot | 424/184 |
| 3,880,996 | 4/1975 | Fisher | 424/184 |
| 3,993,073 | 11/1976 | Zafforoni | 424/431 |
| 4,012,497 | 3/1977 | Schopflin | 424/432 |
| 4,307,095 | 12/1981 | Silvestrini et al. | 514/253 |
| 4,705,798 | 11/1987 | Schoenwald et al. | 514/374 |

FOREIGN PATENT DOCUMENTS 803289 10/1958 United Kingdom .

OTHER PUBLICATIONS

Chem. Abst., 105:232,383(s), (1986)—Korbar-Smid.
Chem. Abst., 105:232,320(u), (1986)—Chien et al.
Chem. Abst., 97:66379(q), (1982)—Silvestrini et al.
Chem. Abst., 99:206,013(j), (1983)—Bonomi et al.
Chem. Abst., 104:200166m, (1986)—Malpassi et al.
Chem. Abst., 106:188,392p, (1987)—Valeri et al.
European Search Report in EPO 881 01032.6.
Chem. Abstract, vol. 104, #174346 Y.
Johansen and Bundgaard, J. Pharm. Sci., 72; 1924, (1983).
Dow Corning 360 Medical Fluid.

Primary Examiner—Douglas W. Robinson
Assistant Examiner—Zuhreh A. Fay
Attorney, Agent, or Firm—Ladas & Parry

[57] ABSTRACT

The present invention relates to novel therapeutic ophthalmic compositions containing polydimethylsiloxane, and a process for preparing such ophthalmic compositions.

5 Claims, No Drawings

OPTHALMIC COMPOSITION

BACKGROUND OF THE INVENTION

In order for a pharmaceutical vehicle to be useful as an ophthalmic vehicle, it is necessary that it be non-irritating to the eye, and non-toxic. In order for it to be most effective it must not blur the vision. For certain drugs, unstable in aqueous solution an oil based vehicle is required. For other drugs, which are water soluble and poorly absorbed, it is possible to promote better bioavailability through the use of an oil vechicle (Biopharm. and Drug Disposite, Vol. 7 page 453, 1986). Nevertheless, known oil based ophthalmic vehicles blur the eye. Known vehicles are edible vegetable oils such as cottonseed oil, soybean oil, coconut oil, rapeseed oil, peanut oil, olive oil, palm oil, palm kernel oil, castor oil, sunflower seed oil, wall flower oil, sesame oil; or mineral oils. None of these previously known oils satisfy the 3 above mentioned criteria; all of these oils, while being non-irritating and toxic, blur the vision.

The present invention provides ophthalmic drugs, in an oil based vehicle which is non-irritating, non-toxic and yet does not blur the vision.

DETAILED DESCRIPTION OF THE INVENTION

It is a discovery of the invention that polydimethylsiloxane at a viscosity of 3-70 centistokes, is useful as a unique ophthalmic vehicle which does not blur vision, is non-toxic and non-irritating to the eye.

Polydimethylsiloxane, at a viscosity of 3-70 centistokes may be combined with various opthalmic drugs to provide novel ophthalmic compositions.

Polydimethylsiloxane of the above mentioned viscosity, may for example be combined with oxazolidine pro-drugs of 3-hydroxy-x-[methylamino T methyl]benzyl alcohol commonly known as phenylephrine, of the formula II

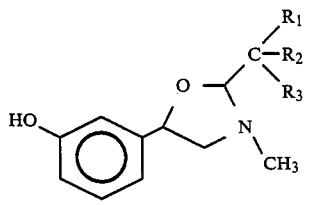

wherein $R_1$, $R_2$, and $R_3$ are any aliphatic combinations of $C_1$-$C_5$, and $R_1$ may also be hydrogen or the non-toxic pharmaceutically acceptable salt forms thereof; to provide a stable, ophthalmic composition.

Phenylephrine is a well-known pharmaceutically active amine whose principal use in the field of ophthalmology is as a mydriatic. There are, however, certain known disadvantages associated with the use of phenylephrine as a mydriatic agent. Those disadvantages have limited the use of this highly effective drug. Thus, in spite of the fact that it is one of the most effective mydriatics available, its use is significantly limited because of the significant side effects which may occur in some individuals treated with phenylephrine. Those unwanted significant side effects range from hypertension, syncope, and even in some cases to myocardial infarction, leading to death. Such side effects have been reported with doses of topical ocular phenylephrine.

One approach which has been used from time to time in the past is the effort to develop successful prodrugs of phenylephrine. The term prodrug refers to a therapeutic agent that requires enzymatic transformation to demonstrate therapeutic activity. In other words, the prodrug itself is not therapeutically active, but once subjected to enzymatic activity by the host organism it is converted to an active drug. In the past there have been some attempts to make prodrugs of phenylephrine, with varying degrees of success. For example, Mindel et al, "Is Phenylephrine Pivalate a Prodrug?", *Arch. Ophthalmol.* 98, 2220 (1980) suggests the reaction product of phenylephrine and pivalic acid to provide a pivalic acid ester as a possible prodrug. However, as reported in that article, phenylephrine pivalate itself produces these side effects. And, it goes without saying that to have a successful prodrug, the prodrug itself must not produce the unwanted side effects, even though it may be effectively converted within the body to the active drug. Johansen et al, "Prodrugs as Drug Delivery Systems XXV: Hydrolysis of Oxazolidines—A Potential New Prodrug Type", *Journal Pharm. Sci.,* 72, 1294 (1983) discloses some prodrug possibilities of ephedrine. However, ephedrine is not commonly used ophthalmically and is biologically different in activity then phenylephrine, with ephedrine being used orally for nacolepsy, bronchial asthma and nasal congestion. In contrast, the oxazolidine derivative of phenylephrine increases the bulk considerably on the amine function, the latter of which is responsible for phenylephrine's activity. With the addition of oxazolidine to the amine function, the prodrug would be expected to be devoid of alpha-adrenergic activity (A. Burger, "Medicinal Chemistry, 3rd ed., *Wiley-Interscience,* 1970, p. 1248).

Accordingly, there is a continuing and real need for safe and effective prodrugs of phenylephrine which can be safely and effectively delivered to the eye.

The prodrug of phenylephrine is not stable in aqueous solution. Thus, it is necessary that effective ophthalmic compositions include the prodrug in an oil suspension.

The composition of the invention is the only manner in which the prodrug can be delivered to the eye in a non-irritating, non-toxic manner without blurring the vision.

Polydimethylsiloxane of a viscosity of 30-70 centistokes may also for example, be combined with the mydriatic drug dapiprazole of the formula III

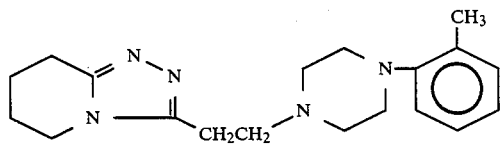

to provide a non-irritating, non-toxic, non-blurring ophthalmic composition.

The compounds of formula II or III themselves, or their base form or pharmaceutically acceptable non-toxic acid salts thereof can be combined with the polydimethylsiloxane with a viscosity of 3-70 centistokes. Such acid salt forms of biologically active compounds which are non-toxic are for example, those derived from inorganic acids such as hydrochloric, hydrobromic, sulfuric, sulfamic, phosphoric, nitric, and the like; and the salts prepared from organic acids such as acetic, propionic, succinic, glycollic, stearic, lactic, malic, tartaric, citric, ascorbic, pamoic, maleic, benzoic, glutamic and salicyclic.

Such pharmaceutically accepted salts of the base form of the compounds of formula II or III in the previously synthesized by conventional, chemical methods. Generally the salts are prepared by reacting the free base form with stoichiometric amounts or with an excess thereof of the desired salt forming inorganic or organic acid, in a suitable solvent, or various combinations of solvents. For example the free base can be dissolved in a mixed aqueous solution of the appropriate acid and the salt recovered by standard techniques, such as evaporation of the solution.

The amount of prodrug in the ophthalmic composition of the present invention can comprise from about 0.00125% by weight of the composition up to about 10% by weight of the composition which is to be topically applied to the eye. Preferably the composition is from about 0.5% by weight of the prodrug of phenylephrine (formula II) or dapiprazole (formula III) up to about 5% by weight of the prodrug or dapiprazole. The balance of the composition is primarily the silicone fluid (polydimethylsiloxane) at a viscosity of 3–70 centistokes.

The pharmaceutical composition, besides the silicone fluid (polydimethylsiloxane) may contain other nontoxic auxiliary substances such as anti-bacterials, antifungals, anti-oxidants, wetting agents, preservatives and the like. Examples include antibacterial components such as chlorobutanol, methyl and propyl paraben, and to the degree they are soluble quaternary ammonium compounds, phenylmercuric salts known to have cold sterilizing properties and which are non-injurious in use, and thimerosal; wetting agents such as pluronic P-103, SPAN with low HLB values (HLB below 5); antifungals such as methyl and propyl paraben; preservatives such as alpha-topoceroland BHA; and other conventional ingredients such as sorbitan monolaurate, triethanolamine oleate, polyoxyethylene sorbitan monopalmitylate, dioctyl sodium sulfosuccinate, monothioglycerol, thiosorbitol, and ethylenediamine tetracetic acid, to the degree they are soluble, and the like.

A source of polydimethysiloxane of a viscosity of 3–70 centistokes is DOW CORNING 360 MEDICAL FLUID. DOW CORNING 360 MEDICAL FLUID can be purchased at a viscosity of 3, 20, 100 centistokes, and to make polydimethylsiloxane of intermediate viscosity one simply appropriately dilutes one viscosity of the DOW CORNING 360 MEDICAL FLUID with another. For example, to obtain a viscosity of 11.5, DOW 360 with a viscosity of 3 and 20 centistokes is mixed 1:1.

The invention also relates to preparing the ophthalmic composition.

Generally, the ophalmic drug of choice is micronized to prevent corneal abrasion. A wetting agent is added to permit interaction between the polydimethylsiloxane and the drug. About 25% of the desired amount of polydimethylsiloxane is mixed with the drug and wetting agent, and the solution is mixed, preferably in a high speed mixer. The remainder of the polydimethylsiloxane is then added. As indicated above, other auxiliary substances may be then added as desired.

An example of typical pharmaceutical composition to be used with the compound 2-t-butyl-3-methyl-5-(m-hydroxyphenly)-1,3-oxazolidine in its base form, includes the following:

| Ingredients | Percent |
| --- | --- |
| 2-t-butyl-3-methyl-5-(m-hydroxyphenyl)-1,3-oxazolidine | 1.00 |
| Chlorobutanol | 0.25 |
| Wetting Agent, Arlacel-85 | 0.05 |
| Dow 360 Medical Fluid, 3 centistokes | Balance |

What is claimed:

1. An ophthalmic composition comprising polydimethylsiloxane with a viscosity of 3–70 centistokkes and a therapeutically effective amount of the ophthalmic drug dapiprazole of the formula

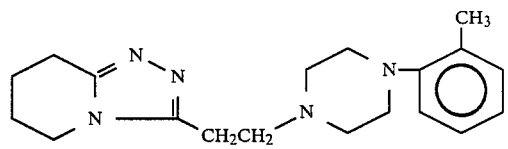

or its non-toxic pharmaceutically acceptable salts thereof.

2. An ophthalmic composition, as in claim 1 further comprising a therapeutically effective amount of one or more of anti-bacterials, antifungals, antioxidants, wetting agents, or preservatives.

3. An ophthalmic composition, as in claim 1 wherein the balance of the composition is primarily polydimethylsiloxane with a viscosity of 3 centistokes.

4. An ophthalmic composition, as in claim 1 wherein the balance of the composition is primarily polydimethylsiloxane with a viscosity of 20 centistokes.

5. A composition as in claim 1 wherein dapiprazole comprises 0.001–10% of the total composition.

* * * * *